(12) United States Patent
Miyamoto et al.

(10) Patent No.: US 7,838,043 B2
(45) Date of Patent: Nov. 23, 2010

(54) SUPEROXIDE ANION DECOMPOSING AGENT

(75) Inventors: Yusei Miyamoto, Tokyo (JP); Naoki Toshima, Tokyo (JP); Takao Asano, Tokyo (JP)

(73) Assignee: Apt Co., Ltd, Shibuya-Ku, Tokyo (JP)

( * ) Notice: Subject to any disclaimer, the term of this patent is extended or adjusted under 35 U.S.C. 154(b) by 1137 days.

(21) Appl. No.: 10/545,750

(22) PCT Filed: Feb. 18, 2004

(86) PCT No.: PCT/JP2004/001817

§ 371 (c)(1),
(2), (4) Date: May 1, 2006

(87) PCT Pub. No.: WO2004/073722

PCT Pub. Date: Sep. 2, 2004

(65) Prior Publication Data

US 2006/0204593 A1   Sep. 14, 2006

(30) Foreign Application Priority Data

Feb. 20, 2003   (JP) .............................. 2003-042452

(51) Int. Cl.
*A61K 33/24* (2006.01)
*A61K 9/14* (2006.01)
*A61P 39/06* (2006.01)

(52) U.S. Cl. ...................... 424/649; 424/489

(58) Field of Classification Search ................. 424/649, 424/489

See application file for complete search history.

(56) References Cited

U.S. PATENT DOCUMENTS

| 5,945,032 | A | 8/1999 | Breitenbach et al. | |
| 6,231,848 | B1 | 5/2001 | Breitenbach et al. | |
| 6,455,594 | B1 | 9/2002 | Tsuji | |
| 6,500,458 | B1 | 12/2002 | Shirahata et al. | |
| 6,814,777 | B2* | 11/2004 | Biberbach | 75/255 |
| 7,588,747 | B2 | 9/2009 | Naito et al. | |
| 2002/0091113 | A1 | 7/2002 | Kazmierski et al. | |
| 2003/0008856 | A1 | 1/2003 | Kazmierski et al. | |
| 2003/0147937 | A1 | 8/2003 | Schwarz | |
| 2004/0154993 | A1 | 8/2004 | Yanagihara et al. | |
| 2005/0170011 | A1 | 8/2005 | Yanagihara et al. | |
| 2007/0090153 | A1* | 4/2007 | Naito et al. | 228/101 |

FOREIGN PATENT DOCUMENTS

| EP | 0832846 | 4/1998 |
| JP | 53-109878 | 9/1978 |
| JP | 59-120249 | 7/1984 |
| JP | 3-243638 | 10/1991 |
| JP | 9-225317 | 9/1997 |
| JP | 10-068008 | 3/1998 |
| JP | 10-176207 | 6/1998 |
| JP | 11-060493 | 3/1999 |
| JP | 11-346715 | 12/1999 |
| JP | 2000-232865 | 8/2000 |
| JP | 2001-010954 | 1/2001 |
| JP | 2001-079382 | 3/2001 |
| JP | 2001-114671 | 4/2001 |
| JP | 2001-145880 | 5/2001 |
| JP | 2002-060805 | 2/2002 |
| JP | 2002-212102 | 7/2002 |
| JP | 2002-241288 | 8/2002 |
| JP | 2003-012523 | 1/2003 |
| JP | 2003-301288 | 10/2003 |
| JP | 2001-122723 | 8/2005 |
| WO | 98/14199 | 4/1998 |
| WO | 99/42112 | 8/1999 |
| WO | 01/76572 | 10/2001 |
| WO | 2004/037019 | 5/2004 |
| WO | 2004/039735 | 5/2004 |

OTHER PUBLICATIONS

HCAPLUS abstract 1998:601181 (1998).*
HCAPLUS abstract 2001:584318 (2001).*
Patent Abstracts of Japan, abstracting JP 2002-212102 (Jul. 2002).*
Machine translation of JP 2002-212102 (Jul. 2002).*
Gendai Kagaku (Chemistry Today), Apr. 1994, feature article.
Tanigoshi, K., "Kyo kara Monoshiri Series—Tokoton Yasashii Mizu no Hon", 1st Edition, Nikkan Kogyo Shimbum, Nov. 2001, pp. 100-124.
English Language Abstract of JP 2003-301288.
English Language Abstract of JP 2003-012523.
English Language Abstract of JP 2002-241288.
English Language Abstract of JP 2002-212102.
English Language Abstract of JP 2001-114671.
English Language Abstract of JP 2001-010954.

(Continued)

*Primary Examiner*—John Pak
(74) *Attorney, Agent, or Firm*—Greenblum and Bernstein P.L.C.

(57) ABSTRACT

A scavenger of superoxide anion or nitric oxide comprising finepowder of a transition metal such as platinum. The scavenger is preferably provided as an aqueous solution containing transition metal colloid at a ratio of 1 mM or less per 1,000 ml, and can efficiently eliminate excessive superoxide anions or nitric oxide in vivo.

6 Claims, 1 Drawing Sheet

OTHER PUBLICATIONS

English Language Abstract of JP 2000-232865.
English Language Abstract of JP 11-346715.
English Language Abstract of JP 11-060493.
English Language Abstract of JP 3-243638.
English Language Abstract of JP 2002-060805.
Yoshida, H.; et al. "Administration of nano-sized platinum colloid reduces the volume of cerebral ischemia by inhibition of increased reactive oxygen species in a rat middle cerebral artery occlusion stroke model", Society for Neuroscience Abstracts, Society for Neuroscience, US, 2003, p. 1.
English Language Abstract of W.I.P.O. 2004/037019.
English Language Abstract of JP 10-068008.
English Language Abstract of JP 59-120249.
English Language Abstract of JP 9-225317.
English Language Abstract of JP 10-176207.
U.S. Appl. No. 10/546,058, filed Aug. 18, 2005.
J. Belloni et al., Heterogeneous Catalysis of Superoxide Anion Dismutation, Radiat. Phys. Chem. vol. 29, No. 2, pp. 89-92, (1987).

* cited by examiner

SUPEROXIDE ANION DECOMPOSING AGENT

This application is a 371 of PCT/JP04/01817, filed on Feb. 18, 2004.

TECHNICAL FIELD

The present invention relates to a scavenger of superoxide anion radical which is one of the reactive oxygen species. The scavenger of superoxide anion radical of the present invention can be used as reduced water or medicaments. The present invention also relates to a scavenger of nitric oxide.

BACKGROUND ART

In the living body, especially in mitochondria, microsomes, leucocytes and the like, a lot of reactive oxygen species (radicals) having high reactivity, such as $O_2^-$ (superoxide anion radical), $H_2O_2$ (hydrogen peroxide), HO. (hydroxyl radical) and $^1O_2$ (singlet oxygen) as an excited molecular species, are generated. It is believed that they are involved in biological regulation including immunological self-defense, biochemical reactions and the like. Nitric oxide (NO) is an unstable short-lived radical species. It has been revealed that this substance also has important functions in a living body as one of the reactive oxygen species (Gendai Kagaku (Chemistry Today), April, 1994, feature article).

In normal cells, the amount of the generation of these reactive oxygen species is approximately 1% of the equivalent amount of the major oxidation-reduction reactions, and they are successively metabolized by catabolic enzymes and the like. The 95% or more of oxygen inhaled by a human by respiration is reduced to water via usual metabolic processes. However, the residue, i.e., some percents of the inhaled oxygen, is left behind as reactive oxygen species oozing from the electron transport systems in mitochondria or microsomes. Most of the reactive oxygen species are eliminated by enzymes for antioxidation such as superoxide dismutase, catalase, and glutathione peroxidase and the like.

However, the reactive oxygen species generated are not completely eliminated by these antioxidation enzymes, and some remained reactive oxygen species result in the oxidation of proteins, lipids, nucleic acids and the like. Although a part of the oxidized substances are restored by other biophylactic mechanisms, substances irreversibly damaged by oxidation are gradually generated. As a result, they are believed to lead to diseases and senescence.

Furthermore, it is well known that expression amounts of antioxidation enzymes such as superoxide dismutase decrease with aging. When the metabolic ability against these oxidized substances becomes insufficient, resulting in accumulation thereof, because of reduced metabolic ability against reactive oxygen species due to senescence as well as because of excessive productions of reactive oxygen species by pathologic conditions, non-specifically oxidized cellular components such as lipids eventually trigger cell death due to the disorders. This phenomenon is one of causes of senescence and various diseases such as Alzheimer's disease.

Examples of diseases in which reactive oxygen species is involved include cancer, diabetes mellitus, atopic dermatitis, Alzheimer's disease, retinitis pigmentosa and the like, and it is considered that excessive state of reactive oxygen species is involved in 90% of human diseases in their certain progression stages. The 90% or more of inhaled oxygen is metabolized in mitochondria, which is the main organelle to generate the reactive oxygen species in a cell. When the balance between the reactive oxygen species generated in mitochondria and the ability of antioxidation system cannot be maintained due to a hereditary disease or aging, the residue of the reactive oxygen species uneliminated will leak from mitochondria to damage the cell, which may induce senescence and cell death due to apoptosis.

As a means for quenching the reactive oxygen species, electrolyzed water with the oxidation reduction potential of −200 to −250 mV at the maximum has been developed as reduced water, and water alkalized by electrolysis to pH 9 to 11 has also been developed (for example, Tanigoshi, K., "Kyo kara Monoshiri Series—Tokoton Yasashii Mizu no Hon (Series of well-informed person from today—Entirely easy book about water)", First edition, Nikkan Kogyo Shimbun, November, 2001, pp. 100-124). Furthermore, it is known that highly active metal fineparticles, e.g., platinum colloid, decompose $H_2O_2$ (hydrogen peroxide), which is one of the reactive oxygen species (for example, Japanese Patent Unexamined Publication (KOKAI) No. 10-68008, paragraph 0040). However, there is no literature reporting that platinum colloid has the quenching ability of superoxide radical or nitric oxide in vivo.

As for methods of production of highly active metal fineparticles, various methods have been known for a long time (for example, Japanese Patent Publication (KOKOKU) Nos. 57-43125, 59-120249, Japanese Patent Unexamined Publication No. 9-225317 and the like).

DISCLOSURE OF THE INVENTION

The inventors of the present invention conducted various researches to provide a means for efficient quenching of $O_2^-$ (superoxide anion) and nitric oxide among the reactive oxygen species generated in a living body and thereby canceling an excessive state of these reactive oxygen species in vivo. The inventors of the present invention focused on transition metal finepowder, especially finepowder of platinum which is one of noble metals, and found that the finepowder successfully invaded into cells and also into mitochondria, and that the finepowder had the ability to scavenge superoxide anion and nitric oxide in mitochondria. The present invention was achieved on the basis of the aforementioned findings.

The present invention thus provides a superoxide anion scavenger comprising finepowders of a transition metal. According to a preferred embodiment, the present invention provides the aforementioned superoxide scavenger, wherein the finepowders of a transition metal is finepowders of a noble metal. This scavenger can quench superoxide anions in vivo.

From another aspect, the present invention provides a nitric oxide scavenger comprising finepowders of a transition metal. According to a preferred embodiment, the present invention provides the aforementioned nitric oxide scavenger, wherein the finepowders of a transition metal is finepowders of a noble metal.

According to preferred embodiments of these inventions, provided are the aforementioned scavengers, wherein the finepowder is finepowders of platinum or finepowders of a platinum alloy; the aforementioned scavengers, which are in an aqueous form containing transition metal colloid; and the aforementioned scavengers, which is in an aqueous form containing the transition metal colloid at a ratio of 1 mM or less in 1000 ml and.

From a still further aspect, the present invention provides a method for eliminating superoxide or nitric oxide in a living body of a mammal including human, which comprises the step of administering finepowder of a transition metal to the living body of the mammal. According to a preferred embodiment of the above invention, water containing transition metal colloid can be administered.

BEST MODE FOR CARRYING OUT THE INVENTION

Figure 1:
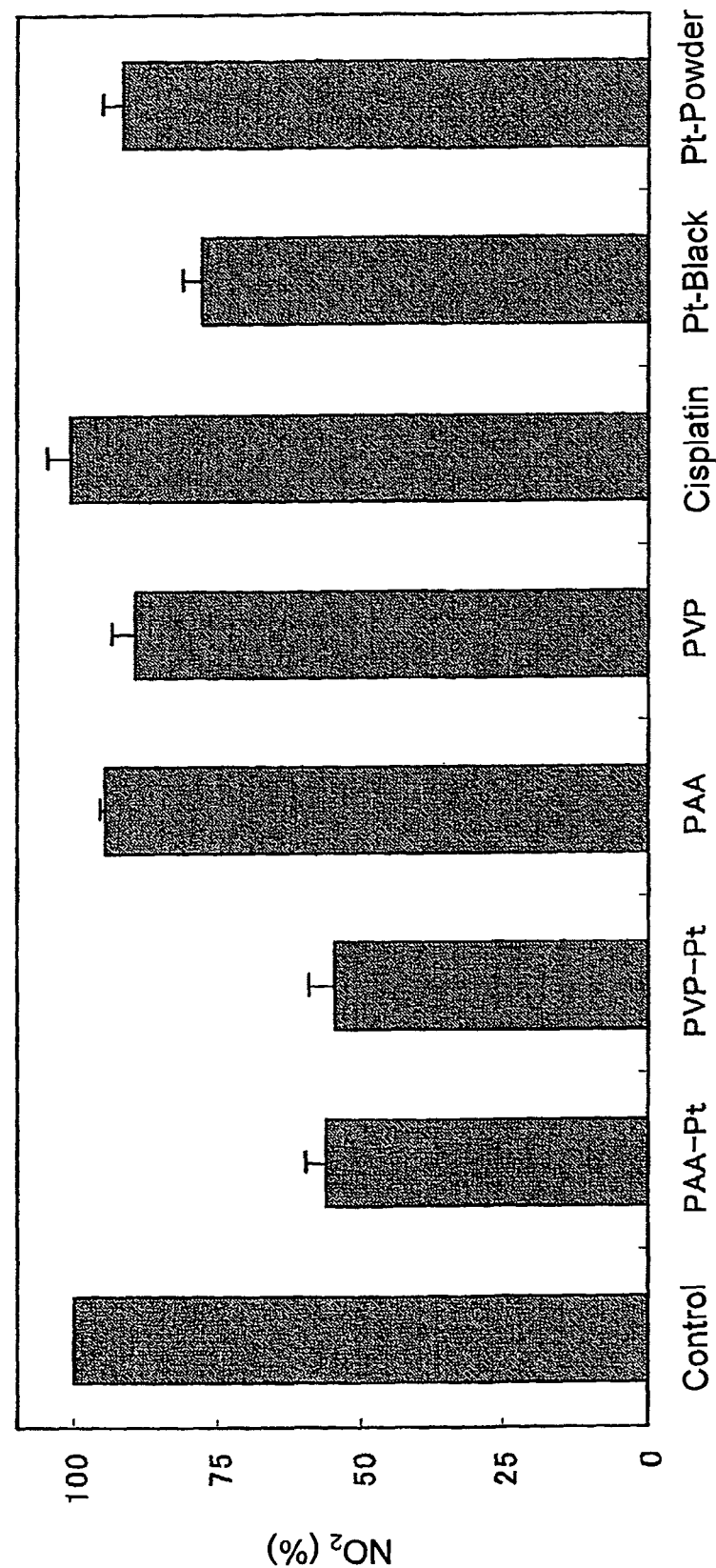
FIG. 1 shows an action of the nitric oxide scavenger of the present invention.

Types of the transition metal used in the scavengers of the present invention are not particularly limited. Specifically, examples of the metal include gold, nickel, platinum, rhodium, palladium, iridium, ruthenium, osmium, and alloys thereof. It is preferred that the transition metal is a noble metal. Types of the noble metal are not particularly limited, and any of gold, ruthenium, rhodium, palladium, osmium, iridium, and platinum may be used. Preferred noble metals include ruthenium, rhodium, palladium, and platinum. A particularly preferred noble metal is platinum. The fineparticles of noble metal may comprise two or more kinds of noble metals. Fineparticles of an alloy containing at least one kind of noble metal, or a mixture containing fineparticles of one or more kinds of noble metals and fineparticles of one or more kinds of metals other than noble metal can also be used. For example, an alloy comprising gold and platinum or the like may be used. Among them, platinum and an alloy of platinum are preferred, and platinum is particularly preferred.

As fineparticles of noble metal, fineparticles that have a large specific surface area and can form a colloidal state that achieves superior surface reactivity are preferred. The sizes of the fineparticles are not particularly limited. Fineparticles having a mean particle size of 50 nm or smaller can be used, and fineparticles having a mean particle size of, preferably 20 nm or smaller, further preferably 10 nm or smaller, most preferably about 1 to 6 nm, can be used. In particular, for the invasion into the inside of mitochondria, the mean particle size is most preferably about 1 to 6 nm. It is also possible to use still finer fineparticles, and such fineparticles are preferred for enhancing uptake thereof into a living body. The scavengers which contain such fineparticles in a stable suspended state in an aqueous medium are also preferred. As the aqueous medium, an organic solvent having low toxicity to a living body and miscible with water at an arbitrary ratio, e.g., ethanol and ethylene glycol, can be used as well as water. As the aqueous medium, water may be preferably used.

Various methods for producing noble metal fineparticles are known (for example, Japanese Patent Publication Nos. 57-43125, 59-120249, Japanese Patent Unexamined Publication (KOKAI) Nos. 9-225317, 10-176207, 2001-79382, 2001-122723, and the like), and those skilled in the art can easily prepare the fineparticles by referring to these methods. For example, as the method for producing noble metal fineparticles, a chemical method called precipitation method or metal salt reduction method, a physical method called combustion method and the like can be used. Fineparticles prepared by any of the methods may be used as the scavengers of the present invention. It is preferable to use fineparticles prepared by the metal salt reduction method from viewpoints of convenience of the production and quality of the fineparticles.

According to the metal salt reduction method, for example, an aqueous solution or organic solvent solution of a water-soluble or organic solvent-soluble noble metal salt or noble metal complex is prepared, and then a water-soluble polymer is added to the solution and pH of the solution is adjusted to 9 to 11, and further the solution can be refluxed by heating under an inert atmosphere to reduce the metal salt or metal complex to obtain metal fineparticles. Types of the water-soluble or organic solvent-soluble noble metal salt are not particularly limited. For example, acetate, chloride, sulfate, nitrate, sulfonate, phosphate and the like can be used, and complexes thereof may also be used.

Types of the water-soluble polymer used for the metal salt reduction method are not particularly limited. For example, polyvinylpyrrolidone, polyvinyl alcohol, polyacrylic acid, cyclodextrin, amylopectin, methylcellulose and the like can be used, and two or more kinds of these polymers may be used in combination. Polyvinylpyrrolidone can be preferably used, and poly(1-vinyl-2-pyrrolidone) can be more preferably used. It is also possible to use various kinds of surface active agents such as anionic, nonionic and lipophilic surface active agents instead of the water-soluble polymer or together with the water-soluble polymer. When an alcohol is used for the reduction, ethyl alcohol, n-propyl alcohol, n-butyl alcohol, n-amyl alcohol, ethylene glycol or the like is used. However, the method for preparing noble metal fineparticles is not limited to the methods explained above.

The metal finepowder prepared by the methods described above is usually obtained in a colloidal state in a solvent used as a medium, and accordingly, the product per se can be used as the superoxide anion scavenger or nitric oxide scavenger of the present invention. When an organic solvent used is removed, the organic solvent can be removed by heating to prepare the scavengers of the present invention in a form of metal finepowders. The metal finepowders obtained by dryness with heating will not lose the characteristic feature as the superoxide anion scavenger or nitric oxide scavenger.

The scavengers of the present invention can be prepared in a form of reduced water. Reduced water means water that has the ability of reducing oxidized substances in vivo. According to the present invention, the reduced water can be prepared that quenches superoxide anion and/or nitric oxide in a dose dependent manner of added scavenger. For example, reduced water dissolving about 0.033 mM of the scavenger per 1,000 ml of water can provide sufficient reducing action, i.e., superoxide anion and/or nitric oxide scavenging action. The reduced water of the present invention preferably contains, for example, the aforementioned scavenger at a ratio of 1 mM or less. By administering reduced water containing the scavenger at the aforementioned ratio to a mammal including human, most of excessive superoxide anions and/or nitric oxide in the living body is quenched.

According to preferred embodiments of the scavengers of the present invention, the scavengers contain metal finepowders having a particle size of a nanometer (nm) order, and after the metal finepowder is administered into a living body, the finepowder is taken up by cells and invade into mitochondria to eliminate superoxide anions generated in the mitochondria or nitric oxide. Therefore, it is expected that the scavengers of the present invention are effective for prophylactic or therapeutic treatment of the aforementioned diseases which are considered to be caused by active oxygen, especially familial amyotrophic lateral sclerosis (FALS), and the like. Moreover, the scavenger of the present invention provided in the form of reduced water can be used as water for drinking or isotonic drink as healthy food, and the scavengers themselves can be used as a medicament or cosmetic, or can also be used for manufacture of healthy food, medicaments, cosmetics and the like.

Furthermore, by blending the nitric oxide scavenger of the present invention in a filter of cigarette or the like, for example, nitric oxide contained in smoke of cigarette can be efficiently decomposed. The scavenger of the present invention can be blended as fineparticles in a solid state, for example, in a filter of cigarette together with activated charcoal or the like or instead of activated charcoal. Alternatively, by filling the scavenger of the present invention in an aqueous colloidal state in a water pipe and introducing smoke of cigarette into the water pipe, nitric oxide contained in the smoke of cigarette can be efficiently eliminated.

EXAMPLES

The present invention will be explained more specifically with reference to the following examples. However, the scope of the present invention is not limited to the following examples.

Example 1

In a 100-ml 2-neck pear-shaped flask connected with an allihn condenser and a 3-neck joint, 0.1467 g of poly(1-vinyl-2-pyrrolidone) as a reagent manufactured by Wako Pure Chemical Industries was placed, and stirred with a stirrer chip for 10 minutes to dissolve in 23 ml of distilled water. Then the mixture was mixed with 2 ml of hexachloroplatinic acid aqueous solution obtained by dissolving hexachloroplatinic acid crystals ($H_2PtCl_6 \cdot 6H_2O$, a reagent manufactured by Wako Pure Chemical Industries) in distilled water so as to have a concentration to $1.66 \times 10^{-2}$ M, and further stirred for 30 minutes. The inside of the reaction system was replaced with nitrogen gas, and the reaction mixture was added with 25 ml of special grade ethanol, and refluxed at a temperature of 100° C. for 2 hours while maintaining the nitrogen gas atmosphere. UV absorbance of the reaction mixture was measured to confirm disappearance of the platinum ion peak and saturation of peak due to scattering peculiar to metal solid, thereby completion of the reduction was confirmed. After the solvent was removed by using an evaporator, the residue was lyophilized over 12 hours to obtain platinum finepowder (scavenger of the present invention).

The resulting scavenger was dissolved in a sodium phosphate buffer at a concentration of 0.1 M, which was adjusted to pH 7.8 beforehand, to obtain dispersions containing the scavenger in a colloidal state at concentrations of 0.66 mM, 0.495 mM, 0.330 mM, 0.165 mM, 0.083 mM, and 0.033 mM. By observation of the dispersions under a microscope, the platinum fineparticles were found to have a particle size of 6 nm or less.

Example 2

By using $O_2^-$ (superoxide anion) generated either from a combination of hypoxanthine/xanthine oxidase or a combination of phenazine methosulfate/NADH (reduced type of nicotinamide adenine dinucleotide), the ability of scavenging superoxide anion of the resulting scavenger was measured as follows.

(A) Hypoxanthine/Xanthine Oxidase System

To a sample container, 20 µl of DMPO (5,5-dimethyl-1-pyrroline N-oxide, spin trap agent produced manufactured by Labtech) having a concentration of 8.8 M, 50 µl of hypoxanthine (Sigma) at a concentration of 1 mM, 50 µl of MilliQ (purified water, Millipore) and 50 µl of each of five kinds of the aforementioned samples at different concentrations were successively added and mixed, and then added with 50 µl of xanthine oxidase (Roche) having a concentration of 0.04 U/ml. After 45 seconds, ESR spectra were measured by using an ESR measuring apparatus (JES-FA200 produced by JEOL Co., Ltd.). The amount of $O_2^-$ (superoxide anion) was measured on the basis of comparison with a standard substance (manganese). The results obtained are shown in Table 1. The numerical values in the parentheses are relative values based on the value at concentration of zero (0) which was taken as 100.

TABLE 1

| Concentration (mM) | Peak value |
|---|---|
| 0 | 5.174 (100.0) |
| 0.083 | 5.044 (97.5) |
| 0.165 | 3.896 (75.3) |
| 0.330 | 3.762 (72.7) |
| 0.495 | 2.987 (57.6) |
| 0.660 | 2.571 (49.7) |

(B) Phenazine Methosulfate/NADH System

For 4 samples among the aforementioned samples (concentration: 0.033 mM, 0.083 mM, 0.165 mM, and 0.330 mM), 20 µl of DMPO at a concentration 8.8 M, NADH (Funakoshi), phenazine methosulfate (Wako Pure Chemical Industries), and 50 µl of each of the aforementioned samples were successively added to a sample container and mixed. After 1 minute, ESR spectra were measured in the same manner as described above. The results are shown in Table 2. The numerical values in the parentheses are relative values based on the value at the concentration of zero (0) which was taken as 100.

TABLE 2

| Concentration (mM) | Peak value |
|---|---|
| 0 | 3.219 ± 0.401 (100.0) |
| 0.033 | 2.146 ± 0.059 (66.7) |
| 0.083 | 0.632 ± 0.360 (19.7) |
| 0.165 | 0 |
| 0.330 | 0 |

Comparative Example 1

Poly(1-vinyl-2-pyrrolidone) without any treatment, or cisplatin ($PtCl_2(NH_3)_2$), which is a platinum complex, was used at the same concentration of poly(1-vinyl-2-pyrrolidone) or platinum as that used in the above examples to measure the amount of $O_2^-$ (superoxide anion). As a result, no difference was observed with reference to the blank (platinum concentration=0).

Example 2

By using $NO_2/NO_3$ Assay Kit-C II (Dojin Chemical Laboratory) as an analysis kit, NO scavenging ability of platinum colloid was examined. This kit is for measuring $NO_2$ produced by hydrolysis of NO. By using a microplate reader (BIO RAD, Model 550), the measurement was carried out 3 times for each sample at a detection wavelength of 570 nm. As the microplate, a 96-well microplate was used. Further, as a NO donor, NOC7 (Dojindo Laboratory) was used. The analysis was conducted basically according to the manual attached to the kit with a little modification. The sample in a volume of 8 µL was added to each well of the microplate, mixed with 84 µL of buffer and 8 µL of NOC7, and left for 30 minutes. The reaction mixture was mixes with 50 µL of reagent A, left for 5 minutes, further mixed with 50 µL of reagent B, and left for 10 minutes, and then detection was performed at a detection wavelength of 570 nm by using a microplate reader. If $NO_2$ generated from NO might react with platinum nanocolloid, disappearance of NO cannot be observed. Therefore, spectrometry was performed by mixing $NO_2$ with platinum nanocolloid. As a result, it was found that no decomposition of $NO_2$ and the like occurred, although the absorbance slightly rose when platinum nanocolloid was contained. NO scavenging ability was analyzed for each sample. The results are shown in FIG. 1. It was proved from these results that platinum nanocolloid had NO scavenging ability.

INDUSTRIAL APPLICABILITY

The superoxide anion scavenger and nitric oxide scavenger of the present invention can decompose excessive superoxide anions and/or nitric oxide in vivo when they are administered to a living body.

What is claimed is:

1. A method for eliminating superoxide anion in a mammal, comprising administering to the mammal platinum fine powder having a particle size of 6 nm or less as observed under a microscope which is prepared by metal salt reduction method in the presence of at least one water-soluble polymer comprising one or more of polyvinylpyrrolidone, polyvinyl alcohol, polyacrylic acid, cyclodextrin, amylopectin, and methylcellulose.

2. The method according to claim 1, wherein the mammal is a human.

3. The method according to claim 1, wherein the metal salt reduction method additionally includes an anionic surface active agent.

4. The method according to claim 2, wherein the metal salt reduction method additionally includes an anionic surface active agent.

5. The method according to claim 1, wherein the platinum fine powder is in an aqueous form comprising platinum metal colloid.

6. The method according to claim 5, wherein the platinum fine powder is present at a ratio of up to 1 mM per 1000 ml.

* * * * *